(12) United States Patent
Lipinski et al.

(10) Patent No.: US 11,786,448 B2
(45) Date of Patent: Oct. 17, 2023

(54) COSMETIC COMPOSITION FOR IMPROVED BLEACHING OR DYEING OF KERATIN FIBERS

(71) Applicant: Kao Corporation, Tokyo (JP)

(72) Inventors: Clarissa Lipinski, Darmstadt (DE); Marine Delbe, Darmstadt (DE)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 17/773,409

(22) PCT Filed: Oct. 30, 2020

(86) PCT No.: PCT/EP2020/080536
§ 371 (c)(1),
(2) Date: Apr. 29, 2022

(87) PCT Pub. No.: WO2021/084082
PCT Pub. Date: May 6, 2021

(65) Prior Publication Data
US 2023/0000747 A1    Jan. 5, 2023

(30) Foreign Application Priority Data
Oct. 31, 2019  (EP) .................................. 19206515

(51) Int. Cl.
| | | |
|---|---|---|
| *A61Q 5/10* | (2006.01) | |
| *A61K 8/58* | (2006.01) | |
| *A61K 8/37* | (2006.01) | |
| *A61K 8/894* | (2006.01) | |
| *A61Q 5/08* | (2006.01) | |

(52) U.S. Cl.
CPC ............. *A61K 8/585* (2013.01); *A61K 8/37* (2013.01); *A61K 8/894* (2013.01); *A61Q 5/08* (2013.01); *A61Q 5/10* (2013.01); *A61K 2800/432* (2013.01)

(58) Field of Classification Search
CPC .......... A61K 8/585; A61K 8/37; A61K 8/894; A61K 2800/432; A61K 2800/31; A61K 2800/882; A61K 8/39; A61K 8/375; A61Q 5/08; A61Q 5/10
USPC ........................................................... 8/405
See application file for complete search history.

(56) References Cited

U.S. PATENT DOCUMENTS

| | | | | |
|---|---|---|---|---|
| 2012/0015048 A1* | 1/2012 | Maitra | ................ | A61K 8/0245 514/772.3 |
| 2017/0087082 A1* | 3/2017 | Doering | ................ | A61K 8/676 |

FOREIGN PATENT DOCUMENTS

| | | | |
|---|---|---|---|
| EP | 0 391 124 A2 | 10/1990 | |
| EP | 1 598 051 A1 | 11/2005 | |
| EP | 2272493 A1 * | 1/2011 | ............... A61Q 5/10 |
| EP | 2272495 A1 * | 1/2011 | ............... A61Q 5/10 |
| EP | 2 606 875 A1 | 6/2013 | |
| FR | 3 059 547 A1 | 6/2018 | |
| JP | 2010-100543 A | 5/2010 | |
| JP | 2019-89749 A | 6/2019 | |

OTHER PUBLICATIONS

International Search Report and Written Opinion dated Feb. 2, 2021 in PCT/EP2020/080536, filed on Oct. 30, 2020, 4 pages.
Partial European Search Report dated Apr. 28, 2020 in European Application 19206515.9, filed on Oct. 31, 2019, 21 pages (with Written Opinion).
Extended European Search Report dated Jun. 22, 2020 in European Application 19206515.9, filed on Oct. 31, 2019, 16 pages (with Written Opinion).
Dipl. Ing. Katrin Steinbach et al. "Utilization of effect pigments in hair colouring formulations", Research Disclosure, Kenneth Mason Publications, vol. 529, No. 6, May 2008, 7 pages.
"Cloisonne™ Vivid Raspberry", IP.Com Journal, IP.com Inc., Feb. 2018, 1 page.
"Isoalkangemisch, dessen Herstellung und Verwendung", IP.Com Journal, IP.com Inc., Nov. 2006, 30 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A cosmetic composition for improved dyeing of keratin fibers is described. The composition comprises alkoxylated organopolysiloxanes and alkoxylated glyceryl esters and/or optionally alkoxylated alkyl glyceryl ethers. The composition may comprise less than 40 wt % water, or may be anhydrous. The composition may further comprise a direct dye, and may be used for bleaching, lightening, or dyeing of keratin fibers.

20 Claims, No Drawings

COSMETIC COMPOSITION FOR IMPROVED BLEACHING OR DYEING OF KERATIN FIBERS

CROSS-REFERENCE TO RELATED APPLICATIONS

The present application is a 35 U.S.C. § 371 national stage application of International patent application PCT/EP2020/080536, filed Oct. 30, 2020, which is based on and claims the benefit of priority to European Application No. 19206515.9, filed Oct. 31, 2019. The entire contents of these applications are incorporated herein by reference.

FIELD OF THE INVENTION

The present invention relates to a cosmetic composition for improved dyeing of keratin fibers. In particular, the deposition of direct dyes on keratin fibers is enhanced. The composition can be employed in bleaching/lightening processes and/or dyeing processes.

BACKGROUND OF THE INVENTION

Bleaching compositions and processes are important tools for fashionable customers to change their hair color, especially from darker to lighter hair shades.

A common disadvantage of bleaching compositions is that the resulting hair color has unintended tones which are strongly disliked by customers. For example, a warm yellow tone is associated with hair of heavy tobacco product users.

For counteracting these unintended color tones, hair direct dyes may be added to bleaching powders (EP1598051).

Bleaching powders are then mixed with aqueous oxidizing compositions yielding a reactive alkaline mixture. This harsh environment challenges the stability of direct dyes.

The prior art has addressed these problems by adding oxidizable solvents to the aqueous bleaching mixture (EP2606875) to stabilize the direct dyes. However, these solvents may add changes to the viscosity of the aqueous bleaching mixture and negatively affect hair feel, resulting in customer dissatisfaction.

The use of organopolysiloxanes and alkoxylated glyceryl esters or optionally alkoxylated alkyl glyceryl ethers alone is generally known in the field of hair care (JP2019-089749, JP2010-100543).

For the reasons laid out above, it is desirable to receive compositions and methods to further stabilize direct dyes under harsh chemical conditions without having further negative effects on the keratin fibers.

SUMMARY OF THE INVENTION

Therefore, the first object of the present invention is a cosmetic composition comprising:
a) one or more alkoxylated organopolysiloxane,
b) one or more compound(s) selected from alkoxylated glyceryl ester(s) and/or optionally alkoxylated alkyl glyceryl ether(s), and/or their mixtures, at a total concentration of 15% by weight or more, calculated to the total weight of the composition,
wherein the composition comprises less than 40% by weight of water, calculated to the total weight of the composition.

The second object of the present invention is a kit-of-parts for bleaching and/or lightening and/or dyeing of keratin fibers, preferably human keratin fibers, more preferably human hair, comprising:

a composition A comprising one or more alkalizing agent(s) and optionally one or more persalt(s) and/or peroxy salt(s),
an aqueous oxidizing composition B,
a composition C as defined above.

The third object of the present invention is a method for bleaching and/or lightening and/or dyeing of keratin fibers, preferably human keratin fibers, more preferably human hair, comprising the steps of:
i) mixing a composition A as defined above with a composition B as defined in the above with a composition C as defined above to yield a ready-to-use composition having a pH in the range of 7 to 12,
ii) applying the ready-to-use composition onto keratin fibers and leaving it for a time period of 1 min to 60 min, preferably for a time period of 5 min to 45 min, more preferably for a time period of 10 min to 30 min,
iii) rinsing-off the keratin fibers with water and optionally shampooing the keratin fibers.

The fourth object of the present invention is a use of a composition as defined above for stabilizing direct dyes in bleaching and/or lightening and/or dyeing processes.

DETAILED DESCRIPTION OF THE INVENTION

The prior art has not yet provided satisfactory solutions to the problems laid out above. Inventors of the present invention have unexpectedly found out that a composition according to claim 1 stabilizes hair direct dyes in ready-to-use bleaching mixtures. As a result, the dyeing ability of the direct dyes is higher and the keratin fibers are more intensely colored. Moreover, the cosmetic properties of the keratin fibers are improved.

Cosmetic Composition

The cosmetic composition of the present invention comprises:
a) one or more alkoxylated organopolysiloxane,
b) one or more compound(s) selected from alkoxylated glyceryl ester(s) and/or optionally alkoxylated alkyl glyceryl ether(s), and/or their mixtures, at a total concentration of 15% by weight or more, calculated to the total weight of the composition,
wherein the composition comprises less than 40% by weight of water, calculated to the total weight of the composition.

Compounds According to a)

The compound according to a) is an alkoxylated organopolysiloxane.

Suitable alkoxylated organopolysiloxanes may be alkoxylated aminated or alkoxylated non-aminated organopolysiloxanes.

Suitable alkoxylated aminated organopolysiloxanes are PEG-x amodimethicones where x is an integer ranging from 2 to 100, PEG/PPG-x/y amodimethicones where x/y are in the range of 2 to 100, or mono- or bisalkyl PEG/PPG-x/y amodimethicones with the same denotation for x and y as before.

It is preferred from the viewpoint of dyeing intensity that the alkoxylated non-aminated organopolysiloxane as compound according to a) is an alkoxylated dimethicone copolymer.

Suitable alkoxylated dimethicone copolymers are PEG-x dimethicone where x is an integer ranging from 2 to 100, PEG/PPG-x/y dimethicone where x/y are in the range of 2 to 100, and mono- or bisalkyl PEG/PPG-x/y dimethicones with the same denotation for x and y as before.

Further examples of such compounds are PEG/PPG-14/4 dimethicone; PEG/PPG-4/12 dimethicone; PEG/PPG-23/6 dimethicone; PEG/PPG-20/23 dimethicone; PEG-12 dimethicone and PEG-8 dimethicone, PEG/PPG-3/10 dimethicone; PEG/PPG-4/12 dimethicone; PEG/PPG-6/4 dimethicone; PEG/PPG-6/11 dimethicone; PEG/PPG-8/14 dimethicone; PEG/PPG-8/26 dimethicone; PEG/PPG-10/2 dimethicone; PEG/PPG-12/16 dimethicone; PEG/PPG-12/18 dimethicone; PEG/PPG-14/4 dimethicone; PEG/PPG-15/5 dimethicone; PEG/PPG-15/15 dimethicone; PEG/PPG-16/2 dimethicone; PEG/PPG-16/8 dimethicone; PEG/PPG-17/18 dimethicone; PEG/PPG-18/6 dimethicone; PEG/PPG-18/12 dimethicone; PEG/PPG-18/18 dimethicone; PEG/PPG-19/19 dimethicone; PEG/PPG-20/6 dimethicone; PEG/PPG-20/15 dimethicone; PEG/PPG-20/20 dimethicone; PEG/PPG-20/23 dimethicone; PEG/PPG-20/29 dimethicone; PEG/PPG-22/23 dimethicone; PEG/PPG-22/24 dimethicone; PEG/PPG-23/6 dimethicone; PEG/PPG-25/25 dimethicone; PEG/PPG-27/27 dimethicone; PEG/PPG-30/10 dimethicone; and/or mixtures thereof.

It is further preferred from the viewpoint of dyeing intensity that the compound according to a) is selected from ethoxylated dimethicone copolymers, propoxylated dimethicone copolymers, and/or ethoxylated/propoxylated dimethicone copolymers, and/or their mixtures.

The most preferred compound from the viewpoint of dyeing intensity and stabilization of direct dyes is PEG/PPG-20/23 dimethicone.

It is preferred from the viewpoint of dyeing intensity and stabilization of direct dyes that the total concentration of compounds according to a) preferably is 1% by weight or more, more preferably is 5% by weight or more, further more preferably 10% by weight or more, calculated to the total weight of the composition.

It is preferred from the viewpoint of dyeing intensity, stabilization of direct dyes, and compound solubility that the total concentration of compounds according to a) preferably is 50% by weight or less, more preferably is 30% by weight or less, further more preferably 20% by weight or less, calculated to the total weight of the composition.

For attaining the above-mentioned effects, the total concentration of compounds according to a) is in the range of 1% to 50% by weight, preferably in the range of 5% to 30% by weight, more preferably in the range of 10% to 20% by weight, calculated to the total weight of the composition.

Compounds According to b)

The composition of the present invention comprises one or more compound(s) selected from alkoxylated glyceryl ester(s) and/or optionally alkoxylated alkyl glyceryl ether(s), and/or their mixtures, at a total concentration of 15% by weight or more, calculated to the total weight of the composition, as compound(s) according to b).

It is preferred from the viewpoint of dyeing intensity and dye stability that one or more compound according to b) is an ethoxylated and/or propoxylated and/or ethoxylated/propoxylated glyceryl ester with linear or branched, saturated or unsaturated $C_8$ to $C_{22}$ fatty acids, preferably with linear or branched, saturated or unsaturated $C_{14}$ to $C_{22}$ fatty acids.

Suitable compounds are PEG-10 olive oil glycerides, PEG-11 avocado oil glycerides, PEG-11 cocoa butter glycerides, PEG-13 sunflower oil glycerides, PEG-15 glyceryl isostearate, PEG-9 coconut fatty acid glycerides, PEG-54 hydrogenated castor oil, PEG-7 hydrogenated castor oil, PEG-60 hydrogenated castor oil, jojoba oil ethoxylate (PEG-26 jojoba fatty acids, PEG-26 jojoba alcohol), glycereth-5 cocoate, PEG-9 coconut fatty acid glycerides, PEG-7 glyceryl cocoate, PEG-45 palm kernel oil glycerides, PEG-35 castor oil, olive oil PEG-7 ester, PEG-6 caprylic acid/capric acid glycerides, PEG-10 olive oil glycerides, PEG-13 sunflower oil glycerides, PEG-7 hydrogenated castor oil, hydrogenated palm kernel oil glyceride PEG-6 ester, PEG-20 corn oil glycerides, PEG-18 glyceryl oleate cocoate, PEG-40 hydrogenated castor oil, PEG-40 castor oil, PEG-60 hydrogenated castor oil, PEG-60 corn oil glycerides, PEG-54 hydrogenated castor oil, PEG-45 palm kernel oil glycerides, PEG-80 glyceryl cocoate, PEG-60 almond oil glycerides, PEG-60 "evening primrose" glycerides, PEG-200 hydrogenated glyceryl palmate, PEG-90 glyceryl isostearate.

It is preferred from the viewpoint of dyeing intensity that that one or more compound according to b) is PEG-7 glyceryl cocoate, PEG-9 cocoglycerides, PEG-40 hydrogenated castor oil and PEG-200 hydrogenated glyceryl palmate.

It is further preferred from the viewpoint of dye stabilization that one or more compound(s) according to b) is an optionally alkoxylated alkyl glyceryl ether having an unsaturated alkyl chain with a total carbon number of 8 or more, preferably having a total carbon number of 9 or more.

It is preferred from the viewpoint of formulation stability that the alkyl chain of compounds according to b) is a straight or branched, saturated or unsaturated alkyl chain having a total carbon number of 18 or less.

For attaining the above-mentioned effect, it is preferred that the alkyl chain of compounds according to b) is a straight or branched, saturated or unsaturated alkyl chain having a total carbon number in the range of 8 to 18, more preferably in the range of 9 to 18.

Suitable examples for compounds according to b) are isostearyl glyceryl ether, stearyl glyceryl ether, isodecyl glyceryl ether, 2-ethylhexyl glyceryl ether, and cetyl glyceryl ether as well as alkyl polyglyceryl ether as disclosed, for example, in EP2003110.

It is preferred from the viewpoint of dyeing intensity that the compounds according to b) are selected from ethoxylated glyceryl cocoate and/or isostearyl glyceryl ether.

It is further preferred from the viewpoint of dyeing intensity and formulation stability that the total concentration of compounds according to b) is 15% by weight or more, further preferably 20% by weight or more, still further preferably 30% by weight or more, calculated to the total weight of the composition.

It is preferred from the viewpoint of solubility that the that the total concentration of compounds according to b) is 80% by weight or less, further preferably 70% by weight or less, still further preferably 65% by weight or less, calculated to the total weight of the composition.

For attaining the above-mentioned effects, it is preferred that the total concentration of compounds according to b) is in the range of 15% to 80% by weight, preferably in the range of 20% to 70% by weight, more preferably in the range of 30% to 65% by weight, calculated to the total weight of the composition.

It is further preferred from the viewpoint of formulation stability that the weight ratio of compounds a) to compounds b) is in the range of 5:1 to 1:5, more preferably in the range of 1:1 to 1:5, still more preferably in the range of 1:2 to 1:4.

Water Content

The composition of the present invention comprises less than 40% by weight of water.

It is preferred from the viewpoint of formulation stability that the composition comprises less than 30% by weight of water, more preferably less than 20% by weight of water, still more preferably less than 10% by weight of water, further more preferably less than 5% by weight of water, still more preferably it is anhydrous.

Direct Dyes

It is one aspect of the composition of the present invention that it comprises one or more direct dye(s).

Preferably, one or more direct dye(s) are selected from anionic, non-ionic, and/or cationic direct dyes.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable non-ionic dyes including nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Suitable cationic dyes are, for this purpose, the ones disclosed in WO 95/15144 of Ciba-Geigy AG. Further examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31, Basic Blue 124.

However, the preferred hair direct dyes are selected from HC Blue 18, HC Red 18, and HC Yellow 16, and/or their mixtures, from the viewpoint of color intensity.

It is preferred from the viewpoint of dyeing intensity that the total concentration of direct dyes in the composition of the present invention is in the range of 0.001% to 10% by weight, more preferably in the range of 0.01% to 8% by weight, further more preferably in the range of 0.1% to 5% by weight, calculated to the total weight of the composition.

In case direct dyes are present in the composition of the present invention, it is preferred from the viewpoint of dyeing intensity that the weight ratio of direct dye(s) to compounds a)+b) is in the range of 1:500 to 1:50, more preferably in the range of 1:250 to 1:75, further more preferably in the range of 1:150 to 1:100.

Optional Ingredients

The composition of the present invention may further comprise one or more organic solvent.

Suitable organic solvents are mono-, di-, and tri-alcohols. Particularly suitable are ethanol, phenoxyethanol, propylene glycol, and glycerol.

In case organic solvents are present, suitable concentration ranges are 1% to 30% by weight, preferably 3% to 20% by weight, calculated to the total weight of the composition.

Kit-of-Parts

The present invention is also directed to a kit-of-parts for bleaching and/or lightening and/or dyeing of keratin fibers, preferably human keratin fibers, more preferably human hair, comprising:

a composition A comprising one or more alkalizing agent(s) and optionally one or more persalt(s) and/or peroxy salt(s), an aqueous oxidizing composition B, a composition C as defined above as inventive composition.

Composition A may be a bleaching powder composition A or an aqueous lightening composition A.

In case composition A is a bleach powder composition, it comprises one or more alkalizing agent(s). Suitable alkalizing agent(s) are metasilicates and disilicates, in particular sodium metasilicate and sodium disilicate. It is preferred from the viewpoint of alkalinity that the total concentration of metasilicates and/or disilicates in the bleach powder composition A is in the range of 1% to 20% by weight, more preferably 5% to 15% by weight, calculated to the total weight of the bleach powder composition A.

Other suitable alkalizing agent(s) are carbonate and bicarbonate alkali salts such as sodium, potassium, and ammonium salts. The preferred salts are bicarbonate salts and especially preferred is ammonium bicarbonate, from the viewpoint of buffer capacity. Suitable concentration of carbonates in the bleach powder composition A is in the range of 0.25% to 10% by weight, preferably in the range of 0.5% to 7.5% by weight, more preferably in the range of 0.75% to 5% by weight, and still more preferably in the range of 1% to 4% by weight, calculated to the total weight of the bleach powder composition before mixing, from the viewpoint of buffer capacity and low hair damage.

Bleach powder composition A may further comprise one or more persalt(s) and/or peroxy salt(s). Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium and ammonium persulfate.

It is preferred from the viewpoint of bleaching power and cosmetic safety that the total concentration of persalts and/or peroxy salts in the bleach powder composition is in the range of 10% to 80% by weight, preferably in the range of 15% to 70% by weight, more preferably in the range of 20% to 60% by weight, and still more preferably in the range of 25% to 60% by weight, calculated to the total weight of the bleach powder composition.

In case composition A is an aqueous lightening composition, it also comprises one or more alkalizing agent(s). In principle, the same alkalizing agent(s) as disclosed above for the bleaching powder composition A are suitable.

The pH of the aqueous lightening composition preferably is in the range of 7 to 12, more preferably in the range of 8 to 11, further more preferably in the range of 8.5 to 10.5.

The aqueous lightening composition A preferably is an emulsion comprising one or more lipophilic compound.

It is preferred from the viewpoint of dyeing intensity that composition A comprises one or more hair direct dye(s), preferably selected from HC Red 18, HC Blue 18, and HC Yellow 16. The hair direct dyes and concentrations as disclosed for the inventive composition are applicable.

Composition B is an aqueous oxidizing composition, preferably comprising hydrogen peroxide, from the viewpoint of cosmetic safety and bleaching/dyeing performance.

From the viewpoint of chemical stability of composition B, the pH preferably is in the range of 1 to 6, more preferably in the range of 1.5 to 5, further more preferably in the range of 2 to 4.

The concentration of hydrogen peroxide in composition B preferably is in the range of 1% to 20% by weight, more preferably in the range of 2% to 15% by weight, further more preferably in the range of 3% to 12% by weight, calculated to the total weight of the composition, from the viewpoint of bleaching/dyeing performance.

Composition C is the composition according to the present invention.

Method for Bleaching/Lightening/Dyeing

The present invention is also directed to a method for bleaching and/or lightening and/or dyeing of keratin fibers, preferably human keratin fibers, more preferably human hair, comprising the steps of:
i) mixing a composition A as defined above with a composition B as defined above with the composition according to the present invention to yield a ready-to-use composition having a pH in the range of 7 to 12,
ii) applying the ready-to-use composition onto keratin fibers and leaving it for a time period of 1 min to 60 min, preferably for a time period of 5 min to 45 min, more preferably for a time period of 10 min to 30 min,
iii) rinsing-off the keratin fibers with water and optionally shampooing the keratin fibers.

The composition A of step i) is then mixed with composition B of step i) and the inventive composition C to form a ready-to-use composition. Suitable mixing ratios by weight for compositions A and B are in the range from 5:1 to 1:5. Furthermore, suitable mixing ratios of (composition A+composition B) to inventive composition C is in the range of 4 to 50. Customarily, suitable example mixing ratios are 1:1:0.5, 1:1.5:0.05, 1:2:0.1, and 1:3:0.1 by weight (composition A:composition B:inventive composition C).

Suitably, the pH of the ready-to-use composition is in the range of 7 to 12. It is preferred from the viewpoint of accelerated bleaching/dyeing that the pH of the ready-to-use composition is in the range of 7.5 to 11, more preferably 8.0 to 10.5.

The ready-to-use composition is then applied to keratin fibers and left for a time period of 1 min to 60 min as defined in step ii). Preferred time ranges for step ii) are 5 min to 45 min, more preferred ranges are 10 min to 35 min, from the viewpoint of sufficiently developing the oxidative hair color or bleaching.

It is further preferred from the viewpoint of dyeing intensity that the weight ratio of direct dye(s) to compounds a)+b) in the ready-to-use concentration is in the range of 1:500 to 1:50, more preferably in the range of 1:250 to 1:75, further more preferably in the range of 1:150 to 1:100.

Optionally, heat may be applied while leaving the ready-to-use composition onto keratin fibers. Suitable temperature ranges are 30° C. to 50° C.

After that, the ready-to-use composition is rinsed-off from keratin fibers according to step iii) and optionally they are shampooed and optionally blow-dried.

Use of the Composition

The present invention is also directed to a use of the inventive composition as defined above for stabilizing direct dyes in bleaching and/or lightening and/or dyeing processes.

The composition of the invention maintains chemical stability under harsh chemical conditions as well as improves deposition of direct dyes onto keratin fibers.

The following examples are to illustrate the present invention, but not to limit it.

EXAMPLES

Example 1

The following composition was prepared by mixing all components and stirring them until complete dissolution:

|  | % by weight |
|---|---|
| PEG/PPG-20/23 dimethicone* | 18.0 |
| PEG-7 glyceryl cocoate** | 58.0 |
| Water | ad 100.0 |

*Silwet L7001E obtained from Momentive Performance Materials Inc.
**Cetiol HE obtained from BASF Corp.

The following bleaching powder composition A was prepared:

|  | % by weight |
|---|---|
| Hydroxyethylcellulose | 3 |
| Tetrasodium EDTA | 2 |
| Sodium carbonate | 1 |
| Ammonium persulfate | 11 |
| Potassium persulfate | 36 |
| Sodium metasilicate | 10 |
| HC Blue 18 | 0.2 |
| Mineral oil | 4 |
| Diatomaceous Earth | ad 100.0 |

The following aqueous oxidizing composition B was prepared:

|  | % by weight |
|---|---|
| Cetearyl alcohol | 4.0 |
| Ceteareth-30 | 1.6 |
| Phosphoric acid | q.s. ad pH 2.5 |
| Tetrasodium EDTA | 0.05 |
| Light mineral oil | 3.0 |
| Hydrogen peroxide | 3.0 |
| Water | ad 100.0 |

The bleaching powder composition A was mixed with the aqueous oxidizing composition B in a weight ratio of 1:2. Then 0.1 parts of the inventive composition were added for form a ready-to-use composition.

As comparative composition the mixture of bleaching powder and aqueous oxidative composition with the same weight ratio of above was used and the inventive composition was replaced with 0.1 part of water.

Wool (2 g per bundle) and human hair streaks (21 cm, 2 g per bundle) were prepared for bleaching experiments and color was measured with a color-difference meter by the CIE colorimetric system (L*,a*,b*) prior to treatment. Then, the ready-to-use compositions were applied and left on the hair streaks for 30 min at 50° C. The compositions were then rinsed off, the keratin fibers were shampooed, and blow-dried. Then Lab values were recorded again.

Based on the (L*,a*,b*) measurements, ΔE was calculated based on the following equation:

$$\Delta E^* = \sqrt{(L^*_1 - L^*_0)^2 + (a^*_1 - a^*_0)^2 + (b^*_1 - b^*_0)^2}$$

| Parameter values | Inventive composition | | Comparative composition | |
|---|---|---|---|---|
| | Human hair | Wool | Human hair | Wool |
| L* | 49.61 | 51.47 | 54.03 | 58.25 |
| a* | 1.63 | 5.79 | 4.34 | 6.88 |
| b* | 10.31 | −16.02 | 14.52 | −6.14 |
| ΔE | 50.70 | 54.21 | 56.12 | 58.98 |

As shown in the experimental results above, color saturation is higher for the inventive composition of about 6 ΔE units on human hair and about 5 ΔE units on wool. Thus, the inventive composition allowed a better deposition of the hair direct dye on keratin fibers during bleaching processes.

Example 2

The following compositions were prepared:

| Ingredients | Inv. comp. 2 | Inv. comp. 3 | Inv. comp. 4 | Comp. comp. 2 | Comp. comp. 3 |
|---|---|---|---|---|---|
| | [% by weight] | | | | |
| PEG/PEG-20/23 dimethicone | 18.0 | — | — | — | — |
| Cetyl PEG/PPG-10/Dimethicone | — | 18.0 | 18.0 | 18.0 | 10.0 |
| PEG-7 glyceryl cocoate | — | 58.0 | — | — | 8.0 |
| Isostearyl glyceryl ether | 58.0 | — | 58.0 | — | — |
| Argan oil | — | — | — | 58.0 | — |
| Propylene glycol | | | Ad 100.0 | | |
| a* | 1.66 | 2.00 | 1.94 | 2.89 | 2.82 |
| b* | 9.92 | 11.92 | 10.39 | 12.88 | 12.77 |

The compositions were mixed with the bleaching powder and oxidizing composition of example 1 using the same protocol. Human hairstreaks were treated with the ready-to-use composition and color results were measured in the same way as explained under example 1.

The lower a* and b* values in comparison to the comparative example illustrate a cooler color shade and better uptake of the blue dye in the bleaching powder. Hence, the customer perceives a color shade with less undesired yellow-tone.

In comparative composition 2 argan oil was used as a representative of natural oils. The composition resembles the one of FR3059547. Apricot kernel oil of the prior art was replaced by argan oil, an equally rich oil of oleic acid and linoleic acid.

Comparative composition 3 illustrated the effect of reducing the concentration of compound(s) according to b).

In all cases, the inventive compositions delivered lower a* and b* values showing the better stabilization if the hair direct dye under oxidative conditions.

Example 3

The following compositions were prepared:

| Ingredients | Inv. comp. 5 | Inv. comp. 6 | Inv. comp. 7 |
|---|---|---|---|
| | [% by weight] | | |
| PEG/PEG-20/23 dimethicone | 50.0 | 50.0 | 30.0 |
| PEG-7 glyceryl cocoate | 30.0 | 50.0 | 60.0 |
| Propylene glycol | | Ad 100.0 | |
| a* | 1.32 | 1.25 | 1.26 |
| b* | 10.86 | 11.69 | 11.44 |

The compositions were mixed with the bleaching powder and oxidizing composition of example 1 using the same protocol. Human hair streaks were treated and color results were measured in the same way as explained under example 1.

In all cases, the inventive compositions delivered low a* and b* values showing the better stabilization if the hair direct dye under oxidative conditions.

Example 4

| | % by weight |
|---|---|
| PEG/PPG-20/23 dimethicone | 18.0 |
| PEG-7 glyceryl cocoate | 58.0 |
| HC Blue 18 | 0.5 |
| HC Yellow 16 | 0.1 |
| HC Red 18 | 0.05 |
| 2-aminomethyl propanol | 0.5 |
| Water | ad 100.0 |

Example 5

| | % by weight |
|---|---|
| PEG/PPG-20/23 dimethicone | 18.0 |
| Isostearoyl glyceryl ether | 50.0 |
| Propylene glycol | 15.0 |
| Water | ad 100.0 |

Example 6

| | % by weight |
|---|---|
| PEG/PPG-20/23 dimethicone | 18.0 |
| Isostearoyl glyceryl ether | 50.0 |
| HC Blue 18 | 0.5 |
| HC Yellow 16 | 0.1 |
| HC Red 18 | 0.1 |
| Water | ad 100.0 |

Example 7

|  | % by weight |
| --- | --- |
| PEG/PPG-20/23 dimethicone | 25.0 |
| Isostearoyl glyceryl ether | 75.0 |

Example 8

|  | % by weight |
| --- | --- |
| PEG/PPG-20/23 dimethicone | 29.35 |
| PEG-7 glyceryl cocoate | 70.0 |
| HC Blue 18 | 0.5 |
| HC Yellow 16 | 0.1 |
| HC Red 18 | 0.05 |

The invention claimed is:

1. A cosmetic composition, comprising:
a) one or more alkoxylated organopolysiloxanes, and
b) one or more compounds selected from the group consisting of an alkoxylated glyceryl ester, an alkoxylated alkyl glyceryl ether, and a mixture thereof, at a total concentration of 15% by weight or more, calculated to the total weight of the composition,
wherein the composition comprises less than 40% by weight of water, calculated to the total weight of the composition.

2. The composition according to claim 1, wherein the compound according to a) is an alkoxylated dimethicone copolymer.

3. The composition according to claim 1, wherein the compound according to a) is at least one selected from the group consisting of an ethoxylated dimethicone copolymer, a propoxylated dimethicone copolymer, an ethoxylated/propoxylated dimethicone copolymer, and a mixture thereof.

4. The composition according to claim 1, wherein the total concentration of compounds according to a) is in the range of 1% to 50% by weight, calculated to the total weight of the composition.

5. The composition according to claim 1, wherein the total concentration of compounds according to a) is in the range of 10% to 20% by weight, calculated to the total weight of the composition.

6. The composition according to claim 1, wherein the one or more compounds according to b) is at least one selected from the group consisting of an ethoxylated glyceryl ester, a propoxylated glyceryl ester, and an ethoxylated/propoxylated glyceryl ester, and
wherein the one or more compounds has linear or branched, saturated or unsaturated $C_8$ to $C_{22}$ fatty acids.

7. The composition according to claim 1, wherein the one or more compounds according to b) is at least one selected from the group consisting of an ethoxylated glyceryl ester, a propoxylated glyceryl ester, and an ethoxylated/propoxylated glyceryl ester, and
wherein the one or more compounds has linear or branched, saturated or unsaturated $C_{14}$ to $C_{22}$ fatty acids.

8. The composition according to claim 1, wherein the one or more compounds according to b) is an optionally alkoxylated alkyl glyceryl ether having an unsaturated alkyl chain with a total carbon number of 8 or more.

9. The composition according to claim 1, wherein the one or more compounds according to b) are selected from ethoxylated glyceryl cocoate and/or isostearyl glyceryl ether.

10. The composition according to claim 1, wherein the total concentration of the one or more compounds according to b) is in the range of 15% to 80% by weight, calculated to the total weight of the composition.

11. The composition according to claim 1, wherein the total concentration of the one or more compounds according to b) is in the range of 30% to 65% by weight, calculated to the total weight of the composition.

12. The composition according to claim 1, wherein the weight ratio of the total weight of the one or more compounds a) to the total weight of the one or more compounds b) is in the range of 5:1 to 1:5.

13. The composition according to claim 1, wherein the composition comprises less than 30% by weight of water, calculated to the total weight of the composition.

14. The composition according to claim 1, wherein the composition is anhydrous.

15. The composition according to claim 1, wherein the composition comprises one or more direct dyes.

16. The composition according to claim 1, wherein the composition comprises one or more direct dyes selected from the group consisting of HC Red 18, HC Blue 18, HC Yellow 16, and a mixture thereof.

17. A kit-of-parts for bleaching, lightening, or dyeing of keratin fibers, the kit-of-parts comprising:
a composition A comprising one or more alkalizing agents and optionally one or more persalts and/or peroxy salts,
an aqueous oxidizing composition B, and
a composition C of the cosmetic composition as defined in claim 1.

18. The kit-of-parts according to claim 17, wherein the composition A comprises one or more hair direct dyes.

19. The kit-of-parts according to claim 17, wherein the composition A comprises one or more hair direct dyes selected from the group consisting of HC Red 18, HC Blue 18, HC Yellow 16, and a mixture thereof.

20. A method for bleaching, lightening, or dyeing of keratin fibers, the method comprising:
i) mixing a composition A comprising one or more alkalizing agents and optionally one or more persalts and/or peroxy salts with a composition B comprising an aqueous oxidizing composition with a composition C of the cosmetic composition as defined in claim 1 to yield a ready-to-use composition having a pH in the range of 7 to 12,
ii) applying the ready-to-use composition onto keratin fibers and leaving the applied ready-to-use composition for a time period of 1 min to 60 min, and
iii) rinsing-off the keratin fibers with water and optionally shampooing the keratin fibers.

* * * * *